(12) United States Patent
Chung et al.

(10) Patent No.: US 8,785,598 B2
(45) Date of Patent: Jul. 22, 2014

(54) COENZYME Q10 NANOPARTICLES, PREPARATION METHOD THEREOF AND COMPOSITION CONTAINING SAID NANOPARTICLES

(75) Inventors: Bong Hyun Chung, Daejeon (KR); Jung Hyun Han, Chungcheongnam-do (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 215 days.

(21) Appl. No.: 13/263,296

(22) PCT Filed: Apr. 6, 2010

(86) PCT No.: PCT/KR2010/002112
§ 371 (c)(1),
(2), (4) Date: Oct. 6, 2011

(87) PCT Pub. No.: WO2010/117199
PCT Pub. Date: Oct. 14, 2010

(65) Prior Publication Data
US 2012/0041178 A1  Feb. 16, 2012

(30) Foreign Application Priority Data
Apr. 6, 2009 (KR) .................. 10-2009-0029620

(51) Int. Cl.
*C07K 14/00* (2006.01)

(52) U.S. Cl.
USPC ............ 530/354; 977/773; 977/896; 530/410

(58) Field of Classification Search
None
See application file for complete search history.

(56) References Cited

U.S. PATENT DOCUMENTS

| | | | |
|---|---|---|---|
| 2006/0233845 A1* | 10/2006 | Lukowski et al. | 424/401 |
| 2007/0053985 A1 | 3/2007 | Ueda et al. | |
| 2009/0017105 A1* | 1/2009 | Khattar et al. | 424/450 |
| 2010/0151037 A1* | 6/2010 | Jiang et al. | 424/499 |

FOREIGN PATENT DOCUMENTS

| | | |
|---|---|---|
| EP | 1591020 A1 | 11/2005 |
| JP | 2004-203812 A | 7/2004 |
| JP | 2004-242509 A | 9/2004 |

OTHER PUBLICATIONS

International Search Report prepared by the Korean Intellectual Property as International Searching Authority for PCT International Patent Application No. PCT/KR2010/002112 mailed Jan. 3, 2011, 2 pages, English.

* cited by examiner

*Primary Examiner* — Anand Desai
(74) *Attorney, Agent, or Firm* — Swanson & Bratschun, L.L.C.

(57) ABSTRACT

Provided are a coenzyme Q10 nanoparticle, a method of preparing the same and a composition having the nanoparticle. According to the present invention, Coenzyme Q10 may be dissolved in only a water-miscible organic solvent, and easily made into a nano-sized particle and solubilized under a low energy condition, for example, by simple stirring. The coenzyme Q10 may be dispersion-stabilized by an amino acid or protein. The coenzyme Q10 is formed in a nano-sized particle and solubilized, an absorption rate may be increased and simultaneously deliver the amino acid and protein with the nanoparticle. Thus, the coenzyme Q10 nanoparticle can be effectively used in food, cosmetics and medicine.

8 Claims, 6 Drawing Sheets

COENZYME Q10 NANOPARTICLES, PREPARATION METHOD THEREOF AND COMPOSITION CONTAINING SAID NANOPARTICLES

CROSS-REFERENCE TO RELATED APPLICATION

This application is a 35 U.S.C. §371 national phase application of PCT/KR2010/002112, filed Apr. 6, 2010 (WO 2010/117199 A2), entitled "Coenzyme Q10 Nanoparticles, Preparation Method Thereof and Composition Containing Said Nanoparticles." PCT/KR2010/002112 claims priority to and the benefit of Korean Patent Application No. 2009-0029620, filed Apr. 6, 2009, the disclosure of which is incorporated herein by reference in its entirety.

BACKGROUND

1. Field of the Invention

The present invention relates to a coenzyme Q10 nanoparticle, a method of preparing the same and a composition having the same.

2. Discussion of Related Art

Coenzyme Q10 is referred to as ubidecarenone, and is a ubiquinone ($C_{59}H_{90}O_4$, molecular weight: 863.34) present in higher animals, having 10 isoprene units on a 2,3-dimethoxy-5-methyl-6-polyprenyl-1,4-benzoquinone side chain. It is known that coenzyme Q10 acts not only as a coenzyme, but also as a vitamin-like material improving oxygen efficiency. In addition, it is reported that coenzyme Q10 is essential to produce adenosine triphosphate in mitochondria, and is reported to improve immunity and to have an effect on a heart disease, hyperpiesia, rheumatic valve disease, alveolitis, etc. Coenzyme Q10 contributes to prevention of congestive heart failure, cerebrovascular occlusion, and side effects of anti-cancer drugs (prevention of cardiogenic dysfunction caused by adriamycin), as well as fatigue recovery, regeneration of energy, and antioxidation of active oxygen in a living organism. Further, it is expected to function as an external skin application, thereby showing an anti-aging effect.

However, coenzyme Q10 is poorly soluble in water, and decreases in stability according to the changes in light, heat or pH. Therefore, various researches are being undertaken to ensure the stability of the coenzyme Q10 and to increase an absorption rate thereof.

Conventional arts solubilizing a water-insoluble ingredient are as follows.

Japanese Patent Publication No. 60-199814 discloses a fatty emulsion using a non-ionic surfactant such as polyethyleneglycol or hydrogenated castor oil polyoxyethylene-(20)-ether and treated with Manton Gaulin-type high pressure homogenizer (500-550 kg/cm$^2$).

European Patent No. 494651B1 and U.S. Pat. No. 5,298,246 disclose a composition that is obtained by dissolving ubiquinone in a milk fat, emulsifying the resulting ubiquinone solution using a fat globule membrane and fractioning particles having a diameter of 1 to 5 μm, thereby improving the absorbability.

In addition, Korean Patent No. 10-0835250 discloses a method of producing a self-emulsifying carrier. Here, the method includes uniformly dissolving a water-insoluble active component in non-polar oil, adding lecithin to polyol or polyhydric alcohol, stirring the resulting solution with a surfactant at an elevated temperature, pre-emulsifying the solution in which the lecithin is uniformly dispersed by adding non-polar oil in which the water-insoluble active ingredient is dissolved, and passing the pre-emulsion through a microfluidizer.

In Korean Patent No. 10-0463167, a method of preparing a percutaneous absorption-type nanoparticle containing coenzyme Q10 as an active ingredient is disclosed, the method including dissolving insoluble polymers, e.g., polymethylmethacrlyate and coenzyme Q10, which are not dissolved in living organisms, in an organic solvent that does not easily mix with water and does not have a particularly high boiling point, for example, dichloromethane, yielding a nanoemulsion through first emulsification in an aqueous solution containing a surfactant and second emulsification using a high pressure emulsifier (pressure: 500 to 1500 bar and flux: 20 to 150 ml/min), removing dichloromethane by solvent extraction and curing the emulsion.

Further, US Patent Publication No. 2008/0160095 discloses a method of preparing a paclitaxel nanoparticle having a size of 160 to 220 nm, the method including dissolving water-insoluble paclitaxel in chloroform, adding the resulting solution to a human-serum albumin aqueous solution and performing first stiffing, preparing a paclitaxel nanoemulsion binding to albumin using a high pressure homogenizer at a high pressure of 9000 to 40000 psi, and removing the organic solvent at 40° C. under a reduced pressure. According to this method, when a water-miscible solvent is individually used, crystalline particles having various sizes from nanometer to micrometer are formed. For this reason, to form only a nano-sized particle, a water-immiscible solvent should be used together with the water-miscible solvent, and a device requiring the use of high energy such as a high pressure homogenizer should be used.

As described above, the conventional methods of solubilizing a water-insoluble active ingredient use various additives, including emulsifying agent, need large amounts of energy and undergo several processes because the methods use warming, primary stiffing and secondary dispersion at a high pressure.

SUMMARY OF THE INVENTION

The present invention is directed to providing a coenzyme Q10 nanoparticle in which a water-insoluble coenzyme Q10 is solubilized and thus an absorption rate is increased.

The present invention is also directed to providing a method of preparing a coenzyme Q10 nanoparticle using a simple process and low energy to increase production efficiency and a composition having the nanoparticle.

One aspect of the present invention provides a coenzyme Q10 nanoparticle binding to at least one or two components selected from the group consisting of amino acids and proteins. Other aspects of the present invention provide a method of preparing a coenzyme Q10 nanoparticle by dissolving coenzyme Q10 only in a water-miscible solvent, adding an amino acid or protein to the resulting solution and removing the water-miscible solvent, and a composition having the coenzyme Q10 nanoparticle.

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which.

DETAILED DESCRIPTION OF EXEMPLARY EMBODIMENTS

Hereinafter, exemplary embodiments of the present invention will be described in detail.

The present invention relates to a coenzyme Q10 nanoparticle binding to at least one or two components selected from the group consisting of amino acids and proteins.

A coenzyme Q10 nanoparticle binding to an amino acid or protein may be obtained by dissolving coenzyme Q10 in a water-miscible organic solvent having an affinity to water, adding the resulting solution to a solution including at least one or two components selected from the group consisting of amino acids and proteins and stiffing the mixed solution, and removing the organic solvent. The binding of the amino acid or protein with the coenzyme Q10 may be physical bonding such as, for example, hydrophobic interaction, hydrogen bonding, electrostatic interaction or van der Waals force. Since the coenzyme Q10 nanoparticle binding to the amino acid or protein is protected by an amino acid or protein, it may be stable and soluble in water and does not agglomerate in an aqueous solution or float on water because of its lower viscosity than water. Accordingly, the present invention provides a coenzyme Q10 nanoparticle which is soluble in water, thereby being easily absorbed by a human body and improved in stability. To prepare a coenzyme Q10 nanoparticle binding to at least one selected from the group consisting of amino acids and proteins, the amino acid and protein may be individually used, or mixed with each other.

In one exemplary embodiment of the present invention, the amino acid may be at least one selected from the group consisting of cysteine and serine.

In another exemplary embodiment of the present invention, the amino acid may further include a water-soluble amino acid. For example, the water-soluble amino acid may be at least one selected from the group consisting of methionine, arginine, glycine, glutamine, threonine, proline, isoleucine, alanine, lysine and glutamic acid.

In another exemplary embodiment of the present invention, the protein may be at least one selected from the group consisting of gelatin, albumin, fibrinogen, lysozyme, silk fibroin, sericin, trypsinogen and pepsin. It is reported that the gelatin or serum albumin has an adsorbing action such as hydrophobic bonding or electrostatic bonding and a function of dispersion-stabilization of a colloid particle in a solution by such an adsorbing action (Lakshmi-narasimhan Krishnamurthy et al. *Journal of Colloid and Interface Science,* 280, 264-275, 2004).

In still another exemplary embodiment of the present invention, the protein may further include a water-soluble protein.

In one exemplary embodiment of the present invention, a content of the amino acid may be 0.5 to 100 parts by weight with respect to 1 part by weight of the coenzyme Q10. When the content of the amino acid is less than 0.5 parts by weight, the amino acid may not sufficiently surround the coenzyme Q10 and thus the coenzyme Q10 may not be stabilized, and when the content of the amino acid is more than 100 parts by weight, the solubilized coenzyme Q10 nanoparticle may not be prepared due to high viscosity.

In still another exemplary embodiment of the present invention, a content of the protein may be 0.5 to 100 parts by weight with respect to 1 part by weight of the coenzyme Q10. When the content of the protein is less than 0.5 parts by weight, the protein may not sufficiently surround the coenzyme Q10 and thus the coenzyme Q10 may not be stabilized, and when the content of the protein is more than 100 parts by weight, the solubilized coenzyme Q10 nanoparticle may not be prepared due to high viscosity.

The present invention also provides a method of preparing a solubilized coenzyme Q10 nanoparticle. The detailed method includes 1) preparing a coenzyme Q10-dissolved mixed solution by dissolving coenzyme Q10 in a water-miscible organic solvent; 2) preparing a coenzyme Q10 nanoparticle binding to at least one or two components selected from the group consisting of amino acids and proteins by adding the mixed solution prepared in 1) to an aqueous solution including at least one or two components selected from the group consisting of amino acids and proteins and stirring the resulting mixture; and 3) removing the water-miscible organic solvent.

Step 1) is characterized by dissolving coenzyme Q10 only in a water-miscible organic solvent without using an emulsifying agent, a surfactant or various additives. The water-miscible organic solvent may be, but is not limited to, one selected from the group consisting of dimethylformamide (DMF), dimethylacetamide (DMAc), N-methylpyrrolidone, pyrrolidone, 1,3-dimethy-3,4,5,6-tetrahydro-2(1H)-pyrimidinone (DMPU), hexamethyl phosphoramide (HMPA), acetone and acetonitrile.

In step 2), when a mixed solution prepared in step 1) is added to an aqueous solution including at least one or two components selected from the group consisting of amino acids and proteins and the resulting mixture is stirred, a water-miscible organic solvent is rapidly diffused into water and coenzyme Q10 binds to an amino acid and a protein, thereby forming a coenzyme Q10 nanoparticle solubilized in the aqueous solution. According to the present invention, the coenzyme Q10 can be solubilized and prepared at a nano-sized level by simple stirring at a low energy level without using a high energy homogenizer or homomixer as used in the conventional art. In one exemplary embodiment of the present invention, the simple stirring may be performed at a speed of 100 to 1000 rpm.

To prepare a solubilized coenzyme Q10 nanoparticle according to the present invention, the amino acid and protein may be individually used, or mixed with each other.

In step 3), the method of removing the water-miscible organic solvent may not be limited to a specific method and a method known in the art may be used. For example, when a volatile solvent is used, a method of evaporating a solvent by stirring, a method of evaporating a solvent by decreasing a pressure or a freeze-drying method may be used. In some cases, an organic solvent may be removed by selectively only separating an organic solvent having a relatively low molecular weight using a molecular weight cut-off membrane filter.

For example, when the water-miscible organic solvent is removed from the coenzyme Q10 nanoparticle binding to a protein, a protein having a large molecular weight, which remains in the aqueous solution, not binding to the coenzyme, may also be purified using the cut-off membrane filter. However, when the cut-off membrane filter is used to remove the water-miscible organic solvent from the coenzyme Q10 nanoparticle binding to an amino acid, amino acids remaining in the aqueous solution, not binding to the coenzyme Q10, have a small molecular weight and thus pass through the cut-off membrane filter. Therefore, the remaining amino acids are not reusable, and thus the freeze-drying of the amino acids is preferred.

The present invention also provides a composition having a solubilized coenzyme Q10 nanoparticle.

In one exemplary embodiment of the present invention, the composition having the solubilized coenzyme Q10 nanoparticle may be a food composition.

A use of the composition is not particularly limited, and thus may be applied to all kinds of food. Examples of the food containing the composition having the coenzyme Q10 nanoparticle may be, but are not limited to, beverages such as soft drinks, sports drinks, carbonated drinks, fruit drinks, lactic drinks, alcoholic drinks, vitamin or mineral drinks, and health drinks; noodles such as udong and spaghetti; bread and snacks such as chocolate, bread, biscuits, candy, and jelly; frozen desserts such as ice cream and ice; processed dairy and meat products such as yogurt and ham; condiments such as soybean paste, sauces, liquid soups, curries, and dressings; processed food such as tofu and the noodles; and processed fat products such as margarine, fat spread, and shortening. In addition, food containing coenzyme Q10 with an additive conventionally used in food may be prepared according to a technique widely known to those of ordinary skill in the art.

In another exemplary embodiment of the present invention, a composition having the solubilized coenzyme Q10 nanoparticle may be a cosmetic composition.

Coenzyme Q10 has antioxidant, anti-inflammatory, fatigue-recovery, skin moisturizing and anti-aging effects, and thus the composition having a coenzyme Q10 nanoparticle can be used in cosmetics. Preparations of the cosmetic composition according to the present invention may include, but are not limited to, softener, emulsion, massage cream, nutrient cream, pack, gel, essence, lipstick, makeup base, foundation, lotion, ointment, gel, cream, cleansing, cleanser, soap, shampoo, rinse, treatment and cosmetic liquid. Such cosmetics may include conventional components such as water-soluble vitamins, oil-soluble vitamins, polypeptides, polysaccharides, or sphingolipids, and may be easily prepared according to a technique widely known to those of ordinary skill in the art. In addition, the above-mentioned component can be properly blended with a conventionally-used additive, such as an antioxidant, a UV protector, an exfoliator, a surfactant, aromatics, a pigment, a preservative, a pH adjuster or a chelating agent.

In still another exemplary embodiment of the present invention, a composition having the solubilized coenzyme Q10 nanoparticle may be a pharmaceutical composition.

Coenzyme Q10 is known to function to promote antioxidant, anti-inflammatory and immunostimulating effects. Thus, a pharmaceutical composition including a coenzyme Q10 nanoparticle binding to at least one component selected from the group consisting of amino acids and proteins of the present invention is not limited to a pharmaceutical composition for treating a specific disease, but may be used as an additional active ingredient for medicine which is expected to have the above-mentioned effects. For example, the composition may be used in, but is not limited to, medicine having effects on a heart disease, hyperpiesia, rheumatic valve disease, alveolitis, congestive heart failure, cerebrovascular occlusion, and side effects of anticancer drugs (prevention of cardiogenic dysfunction caused by adriamycin).

The pharmaceutical composition may be prepared using a pharmaceutically-suitable and physiologically-available adjuvant in addition to an active ingredient, and examples of the adjuvant may include a solubilizing agent such as an excipient, a disintegrating agent, a sweetening agent, a binding agent, a coating agent, an inflating agent, a lubricant, a glossy agent and a flavoring agent.

The pharmaceutical composition of the present invention is preferably formulated to further include at least one pharmaceutically available carrier in addition to the active ingredient to facilitate administration.

Examples of the pharmaceutically available carrier used in the composition formulated in a liquid solution may include saline, sterilized water, Ringer's solution, buffered saline, an albumin injectable solution, a dextrose solution, a maltodextrin solution, glycerol, ethanol and a mixture of one or more components thereof, which are suitable for sterilization and living organisms. When necessary, another conventional additive such as an antioxidant, buffer or bacteriostat may be further added. In addition, the pharmaceutical composition may be formulated in injectable dosage forms such as an aqueous solution, suspension or turbid fluid, a pill, a capsule, a granule, or a tablet by adding a diluting agent, a dispersing agent, a surfactant, a binding agent and a lubricant. Furthermore, the pharmaceutical composition is preferably formulated according to a disease or component using a method disclosed in Remington's Pharmaceutical Science, Mack Publishing Company, Easton Pa., which is a suitable method in the corresponding field.

Types of the dosage form of the pharmaceutical composition of the present invention may be granule, powder, coated tablet, pill, capsule, suppository, syrup, juice, suspension, emulsion, drop or injectable fluid and sustained-release dosage form of an active compound.

The pharmaceutical composition of the present invention may be administered through a conventional route through intravenous, intra-arterial, intraperitoneal, intramuscular, intra-arterial, intraperitoneal, intrasternal, percutaneous, nasal, inhalational, local, rectal, oral, intraocular or intrablood administration.

An effective amount of the active ingredient of the pharmaceutical composition of the present invention means an amount required to have an effect on prevention or treatment of a disease or induction of bond growth. Therefore, the effective amount may be controlled according to various factors including a kind of a disease, severity of a disease, kinds and contents of an active ingredient and other components contained in a composition, a kind of a dosage form, an age, weight, general health condition, sex and diet of a patient, an administration time, an administration route and a secretion rate of a composition, duration of treatment and simultaneously used drugs. For example, for an adult, the effective amount of the coenzyme Q10 may be 1 to 100 mg/kg per day, and the coenzyme Q10 may administered once a day, or administered in divided doses.

The pharmaceutical composition of the present invention may be administered to, but is not limited to, a human, orangutan, chimpanzee, mouse, rat, dog, cow, chicken, pig, goat or sheep.

EXAMPLES

Hereinafter, the present invention will be described in detail with reference to examples to help understanding of the present invention. However, the following examples are merely provided to describe the present invention, not to limit the scope of the present invention. The examples of the present invention are provided to completely explain the present invention to those of ordinary skill in the art.

Example 1

Preparation of Coenzyme Q10 Nanoparticle Solubilized by Cysteine 5 mg coenzyme Q10 was dissolved in 1 ml acetone. The mixed solution was rapidly added to 30 ml of a 1% cysteine aqueous solution stirred at 500 rpm, and dispersed to solubilize coenzyme Q10, and then stirred at 500 rpm for 6 hours to remove a solvent. The aqueous solution in which a coenzyme Q10 nanoparticle was dispersed appeared semi-transparent yellow. The solubilized coenzyme Q10 nanoparticle aqueous solution was stored at 4° C.

Figure 1:
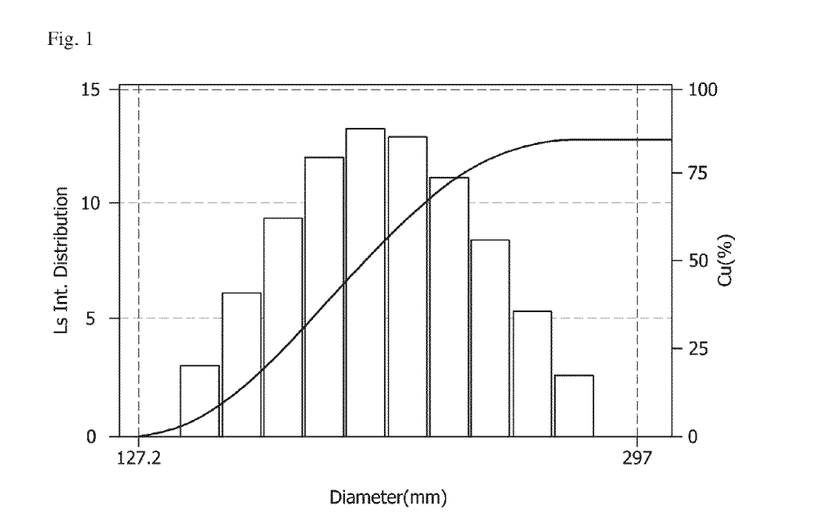
FIG. 1 is a particle distribution curve of a coenzyme Q10 nanoparticle solubilized by cysteine.

FIG. 1 is a particle distribution curve of a nanoparticle of Example 1 measured using a device using laser light scattering (ELS-Z, Otsuka, Japan). It was confirmed that the solubilized nanoparticle had an average particle distribution of 135 to 280 nm.

Example 2

Preparation of Coenzyme Q10 Nanoparticle Solubilized by Serine 5 mg coenzyme Q10 was dissolved in 1 ml N-methylpyrrolidone. The mixed solution was rapidly added to 30 ml of a 1% serine aqueous solution stirred at 500 rpm, and dispersed to solubilize the coenzyme Q10, and then freeze-dried at −20° C. under a reduced pressure for 24 hours using a freeze-drier (EYELA FDU-2100, EYELA, Japan), thereby obtaining a light yellow powder. Afterward, the powder was redispersed in sterilized water, and it was observed that the aqueous solution in which a coenzyme Q10 nanoparticle was dispersed appeared semi-transparent yellow. The solubilized coenzyme Q10 nanoparticle aqueous solution was stored at 4° C.

Figure 2:
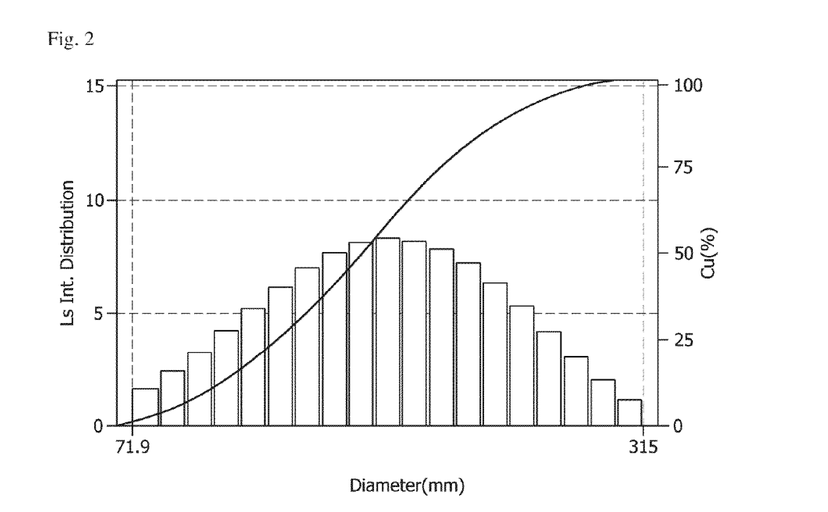
FIG. 2 is a particle distribution curve of a coenzyme Q10 nanoparticle solubilized by serine.

FIG. 2 is a particle distribution curve of a nanoparticle of Example 2 measured using a device using laser light scattering (ELS-Z, Otsuka, Japan). It was confirmed that the solubilized nanoparticle had an average particle distribution of 70 to 315 nm.

Example 3

Preparation of Coenzyme Q10 Nanoparticle Solubilized by Gelatin Extracted from Piscine Skin 10 mg coenzyme Q10 was dissolved in 1 ml N-methylpyrrolidone. The mixed solution was rapidly added to 30 ml of a 1% piscine skin-extracted gelatin aqueous solution stirred at 500 rpm, and dispersed to solubilize the coenzyme Q10. Afterward, an organic solvent having a low molecular weight was removed using a molecular weight cut-off membrane filter and the aqueous solution in which a coenzyme Q10 nanoparticle was dispersed appeared semi-transparent yellow. The solublilized coenzyme Q10 nanoparticle aqueous solution was stored at 4° C.

Figure 3:
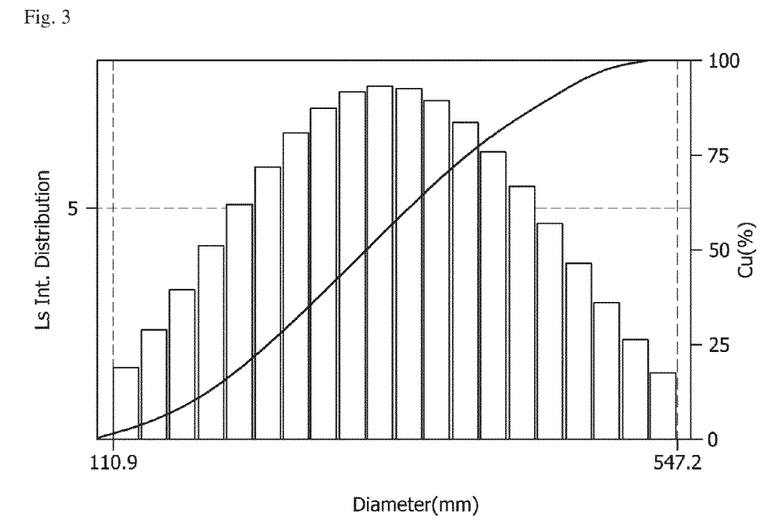
FIG. 3 is a particle distribution curve of a coenzyme Q10 nanoparticle solubilized by gelatin extracted from piscine skin.

FIG. 3 is a particle distribution curve of a nanoparticle of Example 3 measured using a device using laser light scattering (ELS-Z, Otsuka, Japan). It was confirmed that the solubilized nanoparticle had an average particle distribution of 110 to 550 nm.

Example 4

Preparation of Coenzyme Q10 Nanoparticle Solubilized by Gelatin Extracted from Porcine Skin A process was performed as described in Example 3 except that gelatin extracted from porcine skin was used.

Figure 4:
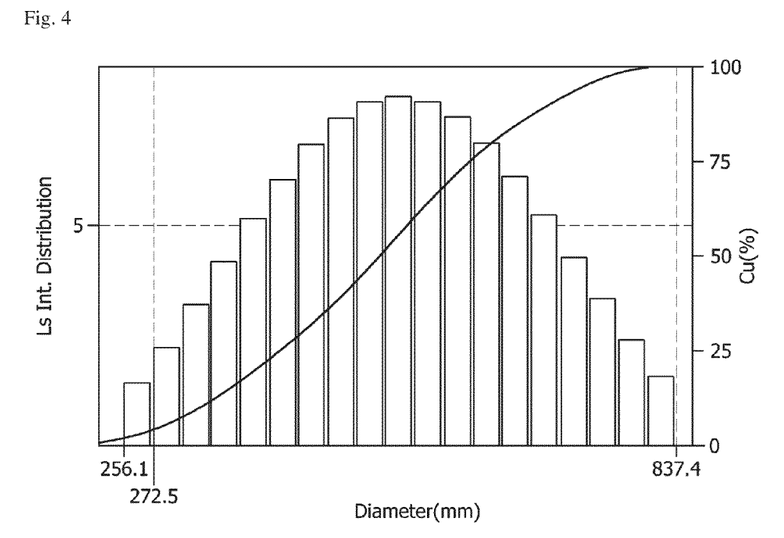
FIG. 4 is a distribution curve of a coenzyme Q10 nanoparticle solubilized by gelatin extracted from porcine skin.

FIG. 4 is a particle distribution curve of a nanoparticle of Example 4 measured using a device using laser light scattering (ELS-Z, Otsuka, Japan). It was confirmed that the solubilized nanoparticle had an average particle distribution of 250 to 850 nm.

Example 5

Preparation of Coenzyme Q10 Nanoparticle Solubilized by Gelatin Extracted from Bovine Skin A process was performed as described in Example 3 except that gelatin extracted from bovine skin was used.

Figure 5:
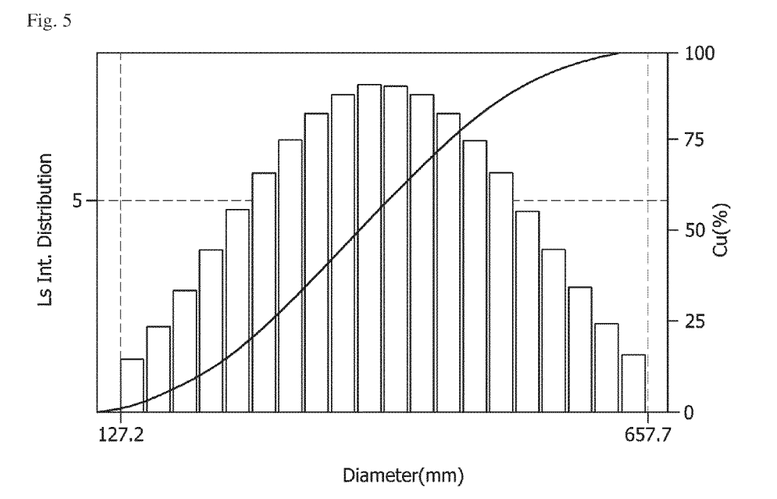
FIG. 5 is a particle distribution curve of a coenzyme Q10 nanoparticle solubilized by gelatin extracted from bovine skin.

FIG. 5 is a particle distribution curve of a nanoparticle of Example 5 measured using a device using laser light scattering (ELS-Z, Otsuka, Japan). It was confirmed that the solubilized nanoparticle had an average particle distribution of 100 to 700 nm.

Example 6

Preparation of Coenzyme Q10 Nanoparticle Solubilized by Egg White Albumin

A process was performed as described in Example 3 except that egg white albumin was used.

Figure 6:
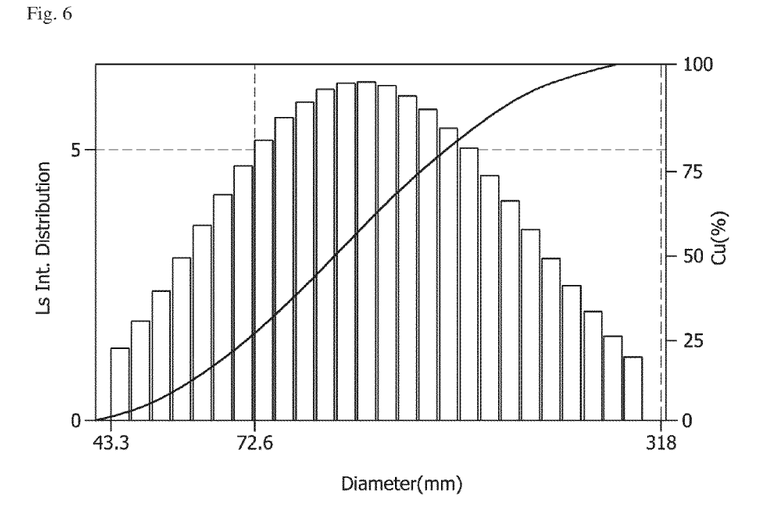
FIG. 6 is a particle distribution curve of a coenzyme Q10 nanoparticle solubilized by egg white albumin.

FIG. 6 is a particle distribution curve of a nanoparticle of Example 6 measured using a device using laser light scattering (ELS-Z, Otsuka, Japan). It was confirmed that the solubilized nanoparticle had an average particle distribution of 40 to 300 nm.

Example 7

Preparation of Coenzyme Q10 Nanoparticle Solubilized by Bovine Serum Albumin

A process was performed as described in Example 3 except that bovine serum albumin was used.

Figure 7:
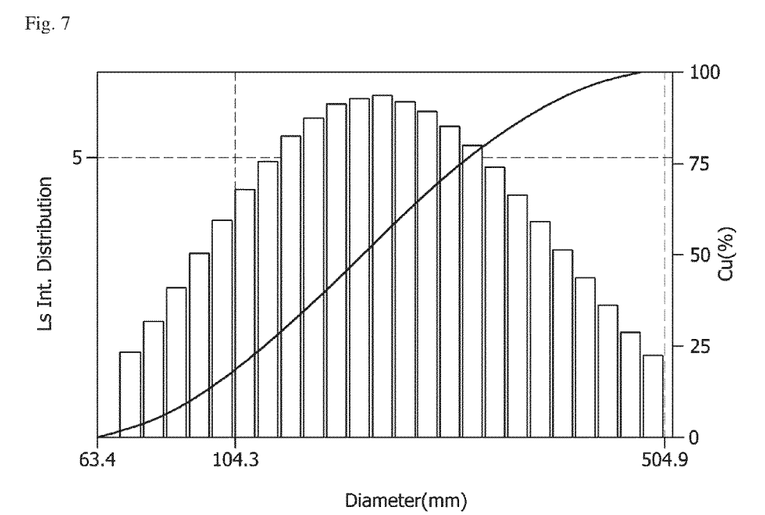
FIG. 7 is a particle distribution curve of a coenzyme Q10 nanoparticle solubilized by bovine serum albumin.

FIG. 7 is a particle distribution curve of a nanoparticle of Example 7 measured using a device using laser light scattering (ELS-Z, Otsuka, Japan). It was confirmed that the solubilized nanoparticle had an average particle distribution of 70 to 500 nm.

Example 8

Preparation of Coenzyme Q10 Nanoparticle Solubilized by Human Serum Albumin

A process was performed as described in Example 3 except that human serum albumin was used.

Figure 8:
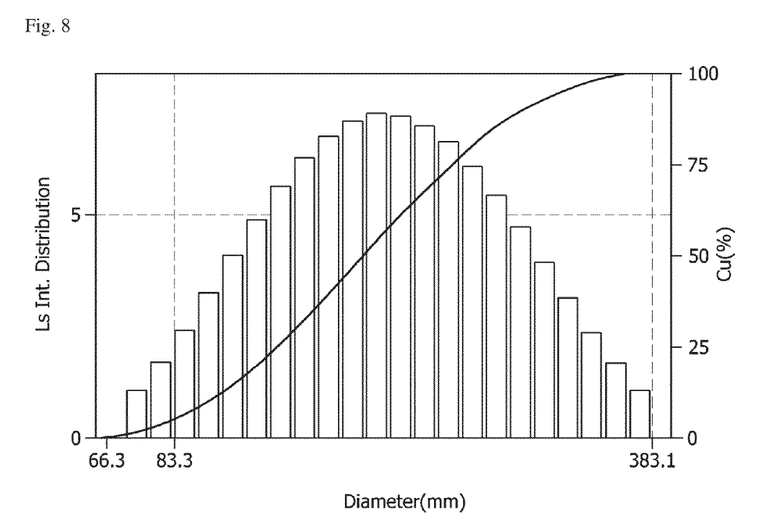
FIG. 8 is a particle distribution curve of a coenzyme Q10 nanoparticle solubilized by human serum albumin.

FIG. 8 is a particle distribution curve of a nanoparticle of Example 8 measured using a device using laser light scattering (ELS-Z, Otsuka, Japan). It was confirmed that the solubilized nanoparticle had an average particle distribution of 70 to 400 nm.

Particle diameters of the nanoparticles prepared in Examples 1 through 8 were measured three cycles using a device using laser light scattering (ELS-Z, Otsuka, Japan). In each cycle, measurement of diameters was performed 100 times. Thus, average particle diameters measured in such a method are shown in Table 1.

TABLE 1

| Sample Name | Average Particle Diameter (nm) | Standard Deviation (±) |
|---|---|---|
| Cysteine (amino acid) | 250.5 | 49.4 |
| Serine (amino acid) | 190.4 | 40.1 |
| Gelatin (extracted from piscine skin) | 223.4 | 5.5 |
| Gelatin (extracted from porcine skin) | 423.9 | 1.5 |
| Gelatin (extracted from bovine skin) | 264.6 | 10.8 |
| Albumin (egg white) | 95.9 | 1.9 |
| Albumin (bovine serum) | 244.2 | 38.6 |
| Albumin (human serum) | 151.3 | 2.7 |

Experimental Example 1

Confirmation of Solubilization of Coenzyme Q10 Nanoparticle

Figure 9:
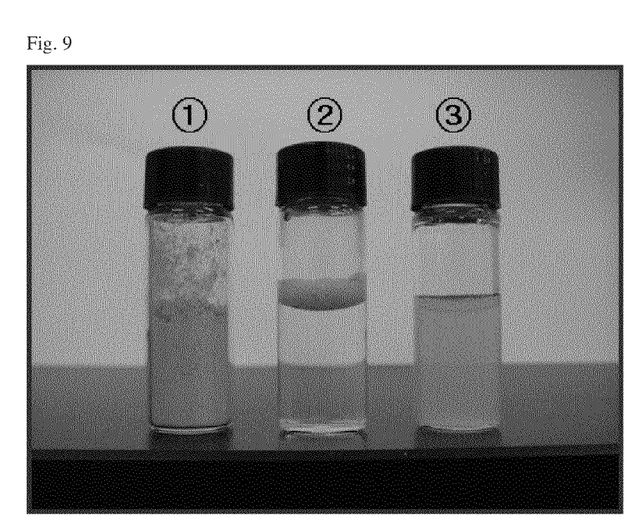
FIG. 9 illustrates images of ① coenzyme Q10 powder, ② an aqueous solution separated into a supernatant layer when coenzyme Q10 is dissolved in water and ③ a semi-transparent yellow aqueous solution formed by solubilizing coenzyme Q10 by bovine serum albumin.

FIG. 9 illustrates images of ① coenzyme Q10 powder, ② an aqueous solution separated into a supernatant layer when coenzyme Q10 is dispersed in water and ③ an aqueous solution of a coenzyme Q10 nanoparticle of Example 7 of the present invention.

As seen from FIG. 9, the insoluble coenzyme Q10, which forms a layer separated from water because it is not soluble in water, was bound to albumin, and thus became water-soluble. As a result, a semi-transparent yellow aqueous solution was formed.

Experimental Example 2

Observation of Coenzyme Q10 Nanoparticle Using Transmission Electron Microscope To observe a shape of the nanoparticle prepared in Example 7, the nanoparticle solubilized by a protein was washed three times at 4° C. at 17000 rpm using centrifugation, and then a sample was prepared for observation using a transmission electron microscope (FE-TEM, JEOL, Japan).

Figure 10:
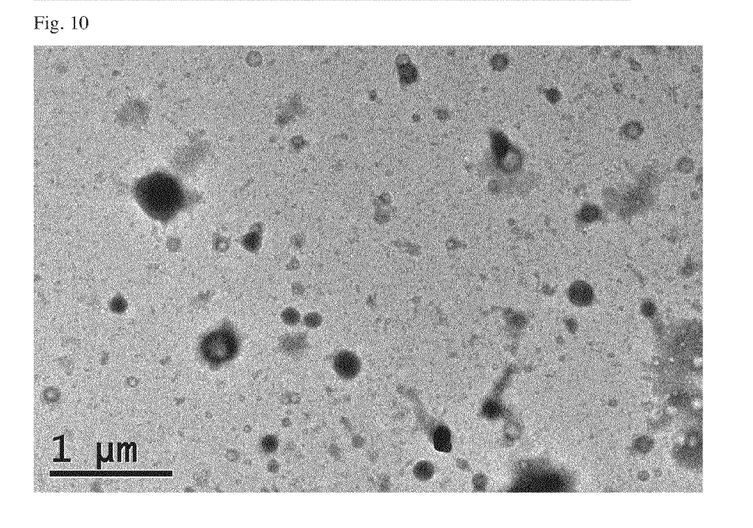
FIG. 10 is a transmission electron microscope (TEM) image of a coenzyme Q10 nanoparticle solubilized by bovine serum albumin.

FIG. 10 is a TEM image of a coenzyme Q10 nanoparticle solubilized by bovine serum albumin It was seen that the coenzyme Q10 nanoparticle surrounded by bovine serum albumin was black.

Experimental Example 3

Confirmation of Stability of Coenzyme Q10 Nanoparticle

To examine long-term stability of a coenzyme Q10 nanoparticle aqueous solution, a semi-transparent yellow aqueous solution prepared by the method described in Example 8 was prepared in three groups, and kept at room temperature for 5 months with UV blocked. Here, an average particle diameter was measured monthly to examine dispersion stability. The experiment was performed under a sterilized condition, and no preservatives or additives were used.

Figure 11:
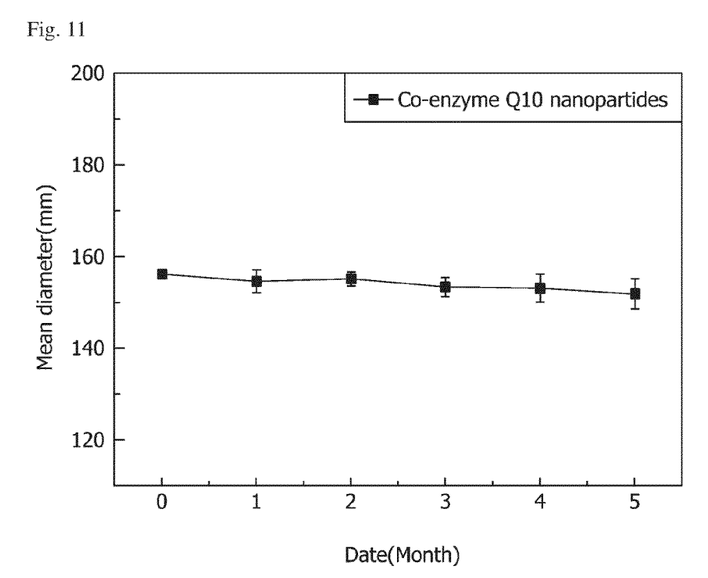
FIG. 11 is a graph illustrating long-term dispersion stability of a coenzyme Q10 nanoparticle solubilized by human serum albumin.

FIG. 11 illustrates long-term dispersion stability of a coenzyme Q10 nanoparticle solubilized by human serum albumin It was confirmed that even after 5 months of the preparation of the coenzyme Q10 nanoparticle, the average particle diameter of the nanoparticle did not significantly change.

Preparation Example 1

Preparation of Transparent Gel-Type Solubilized Dosage Form

In Preparation Example 1, a transparent gel-type solubilized dosage form was prepared in compositions shown in Table 2. A viscosity of the preparation was approximately 4000 cps. Meanwhile, the viscosity was measured at 30° C. at 12 rpm using a Brookfield (LVDVII+).

TABLE 2

| Component (Content: wt%) | Preparation Example 1 |
|---|---|
| Glycerin | 5 |
| Propylene glycol | 4 |
| Coenzyme Q10 Nanoparticle of Example 7 | 5 |
| Ethanol | 10 |
| Sodiumpolyacrylate | 0.5 |
| Preservative | Optimum amount |
| Distilled water | To 100 |

Preparation Example 2

Preparation of Opaque Gel-Type Solubilized Dosage Form

In Preparation Example 2, an opaque gel-type solubilized dosage form was prepared in compositions shown in Table 3. Each of an oil phase preparation and a water phase preparation were completely dissolved at 70° C., and emulsified at 7000 rpm for 5 minutes, thereby preparing an opaque gel-type lotion. A viscosity of the lotion was approximately 2500 cps. Meanwhile, the viscosity was measured at 30° C. at 12 rpm using a Brookfield (LVDVII+).

TABLE 3

| | Component (Content: wt%) | Preparation Example 2 |
|---|---|---|
| Oil Phase | Stearate | 2 |
| | Cetyl Alcohol | 2 |
| | Lanoline Alcohol | 2 |
| | Liquid Paraffin | 7 |
| | Cyclomethicone | 5 |
| | Polyoxyethylene monooleic acid ester | 2 |
| | Preservative, Antioxidant | Optimum Amount |

TABLE 3-continued

|  | Component (Content: wt%) | Preparation Example 2 |
|---|---|---|
| Water Phase | Glycerin 3 | 3 |
|  | Propyleneglycol | 5 |
|  | Triethylamine | 1 |
|  | Coenzyme Q10 Nanoparticle of Example 7 | 10 |
|  | Sodium Polyacrylate | 0.15 |
|  | Distilled water | To 100 |

Preparation Example 3

Preparation of Cream Dosage Form

In Preparation Example 3, a cream dosage form was prepared in compositions shown in Table 4. A preparation process was the same as described in Preparation Example 2.

TABLE 4

|  | Component (Content: wt%) | Preparation Example 3 |
|---|---|---|
| Oil Phase | Bees wax | 2 |
|  | Stearyl Alcohol | 5 |
|  | Stearic acid | 8 |
|  | Squalane | 10 |
|  | Prophylenegycol monostearate | 3 |
|  | Polyoxyethylene cetyl ether | 1 |
|  | Preservative, Antioxidant | Optimum Amount |
| Water Phase | Prophylenegycol | 8 |
|  | Glycerin | 4 |
|  | Triethylamine | 1 |
|  | Coenzyme Q10 Nanoparticle of Example 7 | 10 |
|  | Distilled Water | To 100 |

According to the present invention, coenzyme Q10 can be dissolved in only a water-miscible organic solvent, easily made into a nano-sized particle and solubilized under a low energy condition, for example, by simple stiffing, and dispersion-stabilized by an amino acid or protein. As the coenzyme Q10 is formed in a nano-sized particle and solubilized, an absorption rate may be increased and an amino acid and a protein may be simultaneously delivered with the nanoparticle. Thus, the coenzyme Q10 nanoparticle can be effectively used in food, cosmetics and medicine.

While the exemplary embodiments have been described in detail, it will be understood by those skilled in the art that various changes in form and details may be made therein without departing from the spirit and scope of the invention as defined by the appended claims.

What is claimed is:

1. A method of preparing a solubilized coenzyme Q10 nanoparticle, comprising:
   1) preparing a coenzyme Q10-dissolved mixed solution by dissolving coenzyme Q10 in a water-miscible organic solvent;
   2) producing a coenzyme Q10 nanoparticle binding to at least one or two components selected from the group consisting of amino acids and proteins by adding the mixed solution prepared in step 1) to an aqueous solution including at least one or two components selected from the group consisting of the amino acids and the proteins and stirring the resulting mixture; and
   3) removing the water-miscible organic solvent,
   wherein the amino acid is at least one selected from the group consisting of cysteine and serine;
   wherein the protein is at least one selected from the group consisting of gelatin, albumin, fibrinogen, lysozyme, silk fibroin, sericin, trypsinogen and pepsin; and
   wherein a concentration of the aqueous solution including at least one or two components selected from the group consisting of amino acids and the proteins is 0.001 to 50%.

2. The method according to claim 1, wherein the water-miscible organic solvent is at least one selected from the group consisting of dimethylformamide (DMF), dimethylacetamide (DMAc), N-methylpyrrolidone, pyrrolidone, 1,3-dimethyl-3,4,5,6-tetrahydro-2(1H)-pyrimidinone (DMPU), hexamethyl phosphoramide (HMPA), acetone and acetonitrile.

3. The method according to claim 1, wherein the removing of the water-miscible organic solvent is performed by solvent evaporation by stifling, solvent evaporation under a reduced pressure, freeze-drying or using a cut-off membrane filter.

4. The method according to claim 1, wherein the amino acid further comprises a water-soluble amino acid.

5. The method according to claim 4, wherein the water-soluble amino acid is at least one selected from the group consisting of methionine, arginine, glycine, glutamine, threonine, proline, isoleucine, alanine, lysine and glutamic acid.

6. The method according to claim 1, wherein the protein further comprises a water-soluble protein.

7. The method according to claim 1, wherein a content of the amino acid is 0.5 to 100 parts by weight with respect to 1 part by weight of coenzyme Q10.

8. The method according to claim 1, wherein a content of the protein is 0.5 to 100 parts by weight with respect to 1 part by weight of coenzyme Q10.

* * * * *